(12) United States Patent
Ruetenik

(10) Patent No.: US 10,206,386 B2
(45) Date of Patent: Feb. 19, 2019

(54) EQUINE SHOE

(71) Applicant: Monty L. Ruetenik, Clear Lake City, TX (US)

(72) Inventor: Monty L. Ruetenik, Clear Lake City, TX (US)

(*) Notice: Subject to any disclaimer, the term of this patent is extended or adjusted under 35 U.S.C. 154(b) by 425 days.

(21) Appl. No.: 15/051,343

(22) Filed: Feb. 23, 2016

(65) Prior Publication Data

US 2016/0165871 A1 Jun. 16, 2016

Related U.S. Application Data

(63) Continuation-in-part of application No. 14/046,751, filed on Oct. 4, 2013, now abandoned.

(60) Provisional application No. 62/264,935, filed on Dec. 9, 2015.

(51) Int. Cl.
- *A01L 3/02* (2006.01)
- *A61D 9/00* (2006.01)
- *A61F 5/058* (2006.01)

(52) U.S. Cl.
CPC .............. *A01L 3/02* (2013.01); *A61D 9/00* (2013.01); *A61F 5/0585* (2013.01)

(58) Field of Classification Search
CPC ......... A61F 5/0585; A61D 9/00; A61D 99/00; A01L 1/00; A01L 1/02; A01L 1/04; A01L 3/00; A01L 3/02; A01L 3/04; A01L 3/06; A01K 13/006; A01K 13/007
See application file for complete search history.

(56) References Cited

U.S. PATENT DOCUMENTS

| | | | | |
|---|---|---|---|---|
| 438,952 A | * | 10/1890 | Schatz | A01L 7/00 168/20 |
| 4,346,762 A | * | 8/1982 | Tovim | A01L 3/02 168/17 |
| 4,892,150 A | * | 1/1990 | Thoman | A01L 3/00 168/20 |
| 6,192,989 B1 | * | 2/2001 | Tooman | A01K 13/007 168/1 |
| 6,560,951 B1 | * | 5/2003 | Wood | A01K 13/007 168/18 |
| 2010/0031614 A1 | * | 2/2010 | Osborne | A01K 13/007 54/82 |
| 2017/0027150 A1 | * | 2/2017 | Ruetenik | A01K 13/007 |

* cited by examiner

*Primary Examiner* — Tarla R Patel
(74) *Attorney, Agent, or Firm* — Douglas Baldwin; Timothy Snowden

(57) ABSTRACT

An easily attachable and detachable equine shoe that is made up of a solid member with fabric straps extending from at least two sides that can be secured to an equine hoof. The straps may be folded upward in a plane perpendicular to the top face of the solid member to attach to an equine hoof.

20 Claims, 5 Drawing Sheets

EQUINE SHOE

CROSS-REFERENCE TO RELATED APPLICATION

This application is a continuation in part of application Ser. No. 14/046,751, filed Oct. 4, 2013, published as 2015/0088042, and claims the benefit and priority from U.S. Provisional Patent Application 62/264,935 filed Dec. 12, 2015, the contents and disclosure of which is incorporated herein by reference for all purposes.

FIELD OF THE INVENTION

This invention pertains to equine shoes and specifically to a detachable shaped molded bottom shoe that is easily applied and that allows an equine to find a naturally comfortable position.

BACKGROUND

The patent application from which this application is a continuation in part discloses an equine leg cast bottom attachment comprising a solid member having a top and a bottom and having malleable metal, plastic or fabric straps that may be contoured into a cast, where the straps extend from at least two sides of the bottom of the solid member. The straps may be bent or folded upward in a plane perpendicular to the top face of the solid member to attach to an equine leg cast.

The disclosed system provides a high degree of consistency so that the level of care provided to the equine can be made without the services of an expensive podiatrist or specialist or outsourcing the patient to a referral clinic. It is cost effective and provides consistency and repeatability. The sloped sloe of the system provides a rocker effect that helps protect and stabilize the leg cast and provides more secure and natural footing for equines with leg cast. The sloped rocker bottom on the cast protector allows an equine to find a comfortable position by allowing rotation and by reducing turning torque on the hoof.

The system disclosed in the parent application for protection of equine leg cast performs equally well as a detachable equine shoe that is economical, easily attached and provides great flexibility in positioning and adjustment.

DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION

In broad aspect this invention is an easily attachable and detachable equine shoe. More specifically, it is, in one aspect, an equine shoe comprising a solid member having a top and a bottom and having fabric straps extending from at least two sides of the bottom of the solid member that may be secured to an equine hoof. The straps may be folded upward in a plane perpendicular to the top face of the solid member to attach to an equine hoof.

Figure 1:
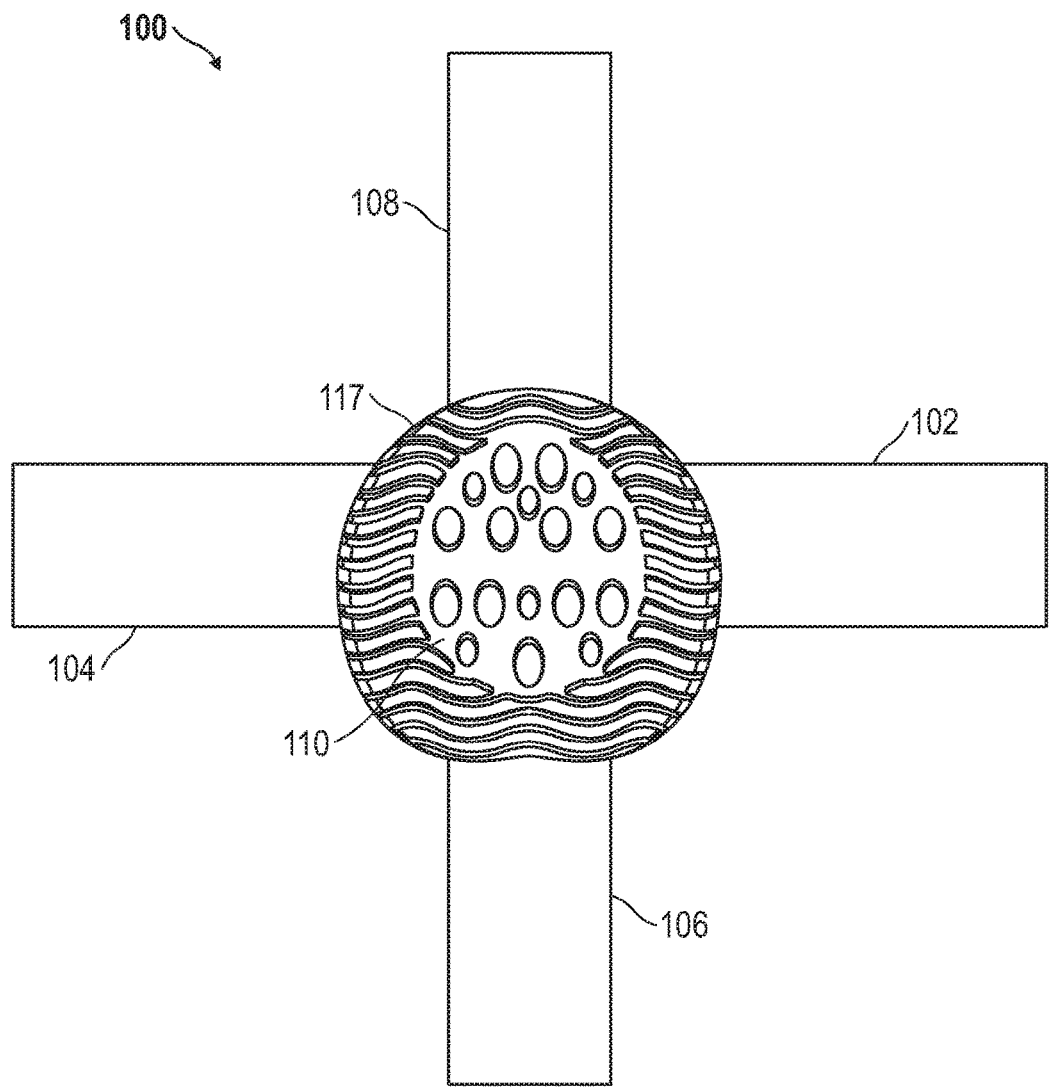
FIG. 1 is a bottom view of an embodiment of the invention showing the solid member with fabric straps.
Figure 2:
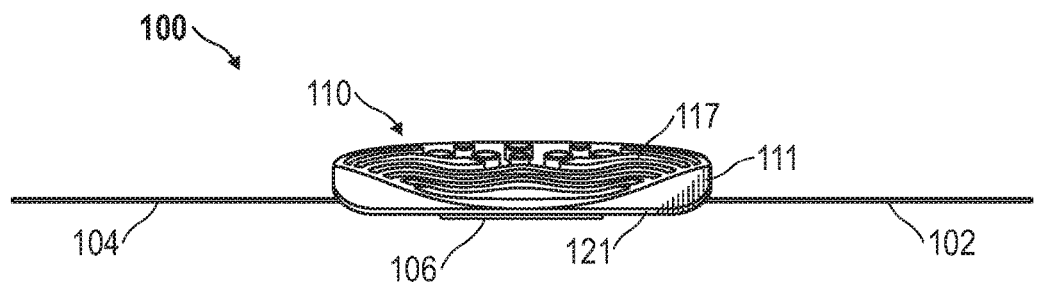
FIG. 2 is a front edge view of an embodiment of the invention.
Figure 3:
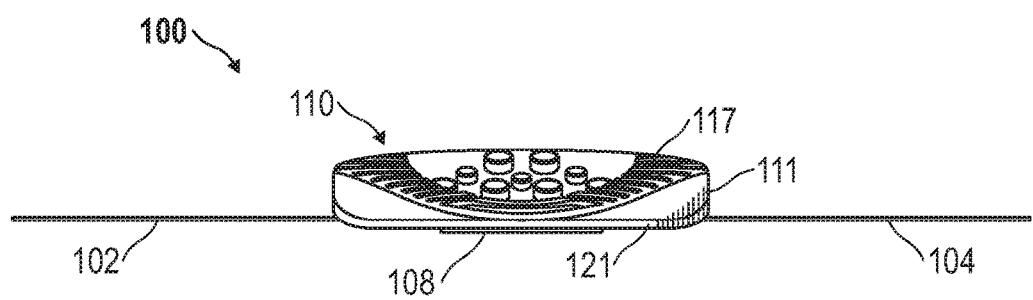
FIG. 3 is a rear edge view of an embodiment of the invention.
Figure 4:
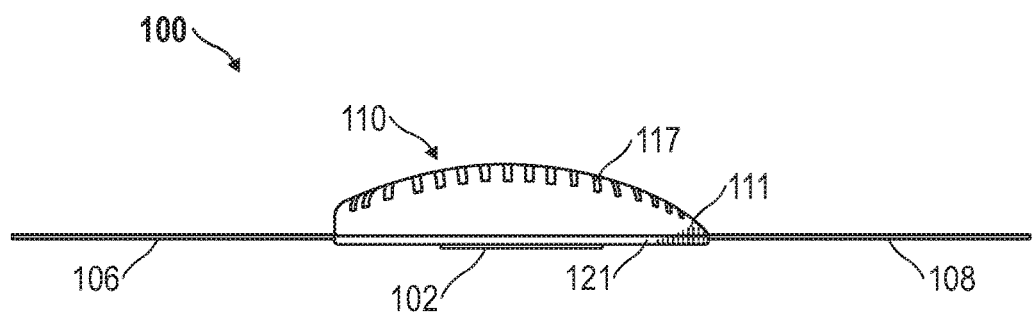
FIG. 4 is a side edge view of an embodiment of the invention.
Figure 10:
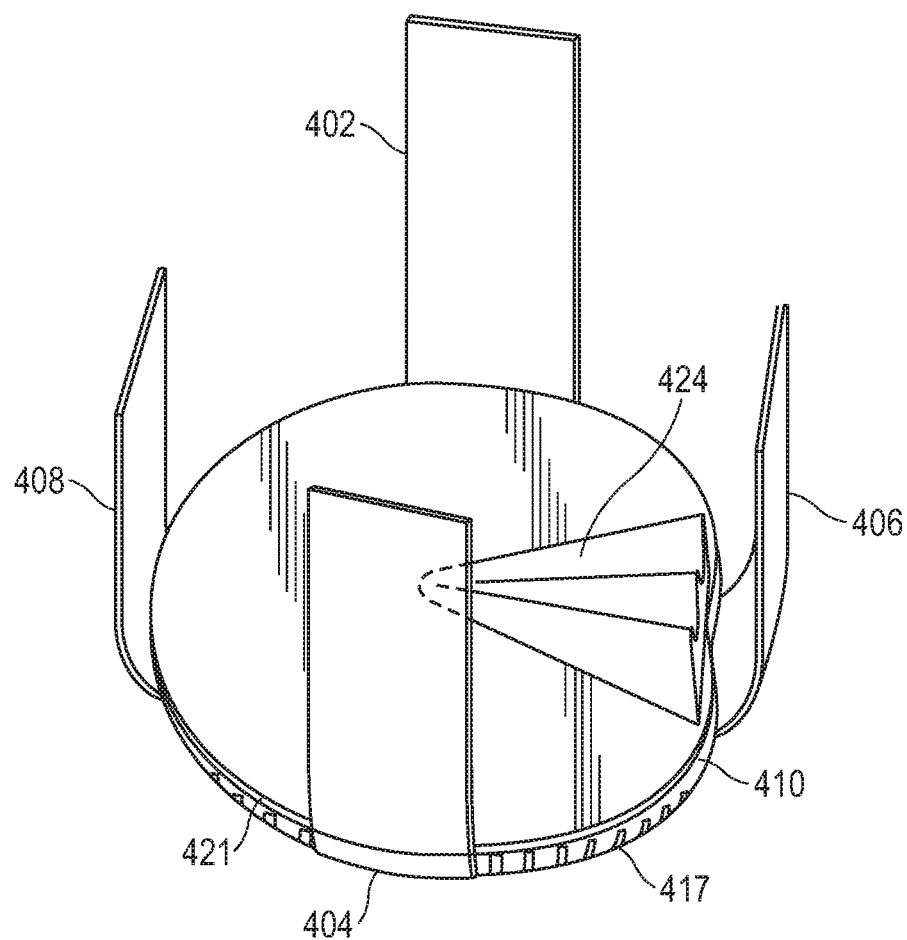
FIG. 10 is a perspective view of an embodiment of the invention showing a frog support.

Referring to the Figures, FIG. 1 shows a bottom view of an embodiment, 100, of the invention. As shown in FIG. 1 there is a solid member, 110. The solid member had two sections, a hard top layer, 121, and a softer lower section 111. Each section has a top side and bottom side, the bottom section 111, being intended to be in contact with the ground when the device is attached to a leg cast. The bottom of the lower section (111) is patterned i.e. cleated or ridged to provide more secure footing and stable contact with the ground or surface on which the equine stands. A suitable cleated design is shown in U.S. Pat. No. 7,178,321, the relevant disclosure of which is herein incorporated by reference. A very suitable patterned design for the bottom of the sole plate is shown in FIG. 10 and in Design Pat. D565, 256, issued Mar. 25, 2008, the disclosure of which is herein incorporated by reference. This design allows for excellent traction by the slanted ridges (117 and 417 in the Figures) on the front and rear of the sole and more flexibility in the center. This flexibility provides more comfort for a horse with an injured or diseased hoof. Other designs and cleat arrangement will be well within the skill on those in the art.

The solid member, 110, may be of any suitable moldable material and molded polymer material such as polyurethane is preferred.

Fabric straps 102, 104, 106 and 108 are attached to the solid member as shown. The straps are fashioned into a molded polymer member about a ¼ inch from the top surface of the solid member, 110, preferably below the harder upper section 121. The straps may be attached to the solid member in any number of ways but are preferably attached near the top (in the upper half of the member) as illustrated in the Figures. The straps on opposite sides of the base 110 may be a single strip of fabric that extends across or through the solid base and extends out on opposites sides. Thus, if the solid member is molded polymer, straps can be laid in the top of the mold, extending out from each side of the mold and the polymer poured into the mold to set, resulting in a solid member with two side straps for each strip of strap material. If the solid member is a completed structure prior to attaching the straps, for example if the solid member is pre-molded polymer, the straps may be attached by any suitable conventional means, such as with screws, nails, adhesive or insertion through a slot in the solid member and similar means.

Figure 5:
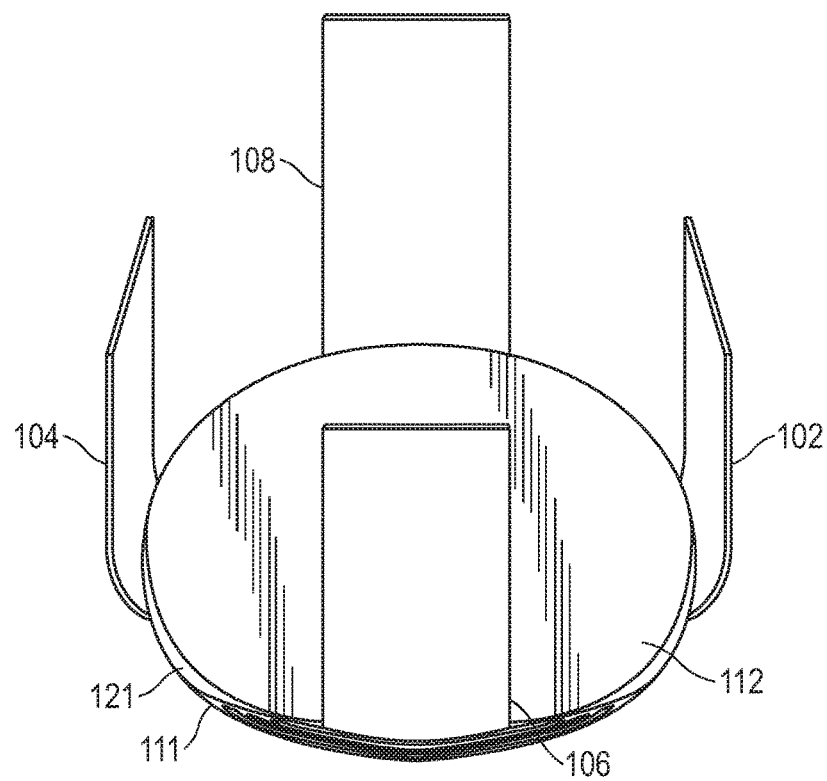
FIG. 5 is a top perspective view of an embodiment of the invention with fabric straps folded upward in position to attach to an equine hoof.
Figure 6:
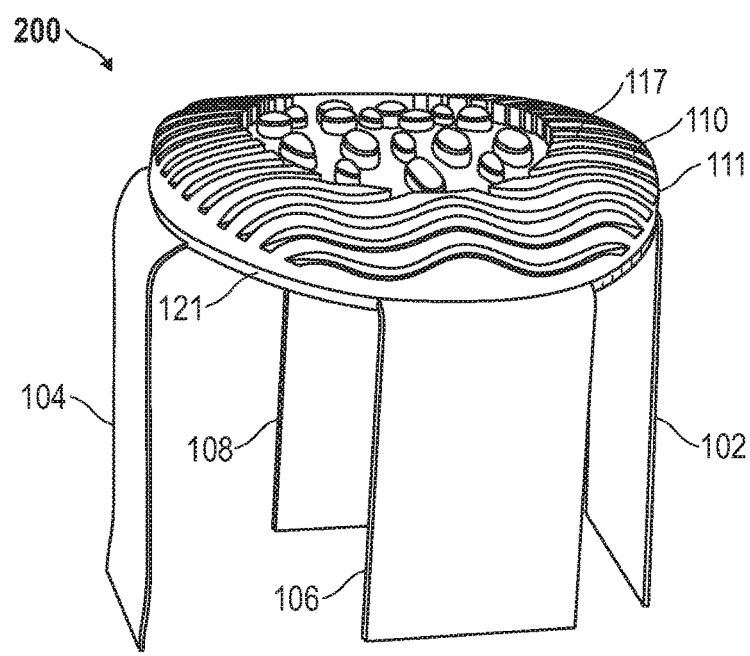
FIG. 6 is a bottom perspective view of an embodiment of the invention with four fabric straps folded upward in position to attach to an equine hoof.

FIGS. 5 and 6, illustrate the straps folded up and contoured to fit a leg/hoof—FIG. 6 shows the cast support inverted from normal positioning on an equine leg in order to illustrate the patterned bottom. FIG. 5 shows an embodiment as it is presented in use as on an equine hoof The fabric straps are suitably made of strong fabrics such as nylon ballistic cloth or ultra-high-molecular-weight polyethylene fabrics (Dynema™ or Spectra™). In general, it is preferred that the cloth or fabric straps be longer than the metal straps. Lengths extending from the molded bottom will be 3 to 14 inches and preferably about 6 to 12 inches. Width can vary from about one inch to about 6 inches. Wider widths can be split to provide more flexibility in wrapping them into the cast material.

Nylon ballistic cloth is generally very tough and durable fabric made with a "ballistic weave", typically a 2×2 or 2×3 basket weave. It can be woven from nylon yarns of various denier such as 840 denier and 1680 denier.

Other particularly suitable fabrics include Dyneema™ and Spectra™. Dyneema and Spectra™ are Ultra-high-molecular-weight polyethylene fabrics that are gel spun through a spinneret to form oriented-strand synthetic fibers with yield strengths as high as 2.4 GPa (350,000 psi) and specific gravity as low as 0.97 (for Dyneema SK75). High-strength steels have comparable yield strengths, and low-carbon steels have yield strengths much lower (around 0.5 GPa). Since steel has a specific gravity of roughly 7.8, this gives strength-to-weight ratios for these materials in a range from 10 to 100 times higher than steel. Strength-to-weight ratios for Dyneema are about 40% higher than for aramid.

FIGS. 2, 4, 7, 8 and 9 are side and end views of a solid member base that is tapered to form a molded rocker configuration. These Figures show the way the solid member may be tapered and the way the straps are molded in near the top side of the member The tapers of the molded shoe may be varied to provide the type rocker action desired. The sole shape illustrated in FIGS. 1-6 is sloped to the front and sloped to the rear. This allows maximum flexibility of movement and allows the horse more options to find the optimum comfortable position but is least stable of the configurations. This sole shape is useful to enhance self-stretching of ligaments as when preparing for exercise, much like a person stretching the Achilles tendons by leaning on a wall before a run.

Figure 7:
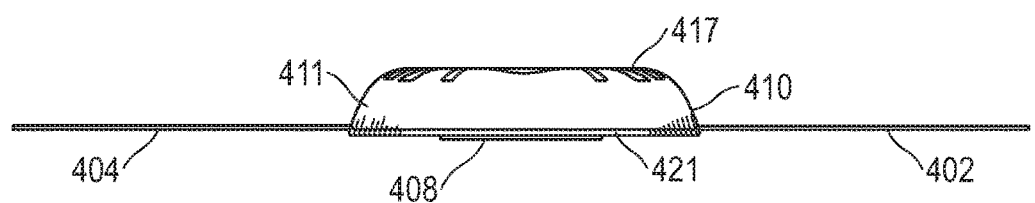
FIG. 7 is a rear view of an embodiment of the invention with four fabric straps.
Figure 8:
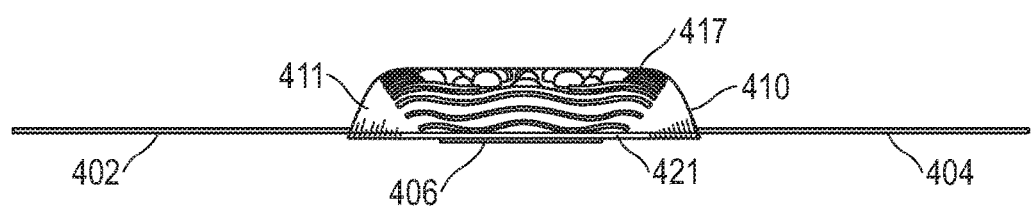
FIG. 8 is a front view of an embodiment of the invention with four fabric straps.
Figure 9:
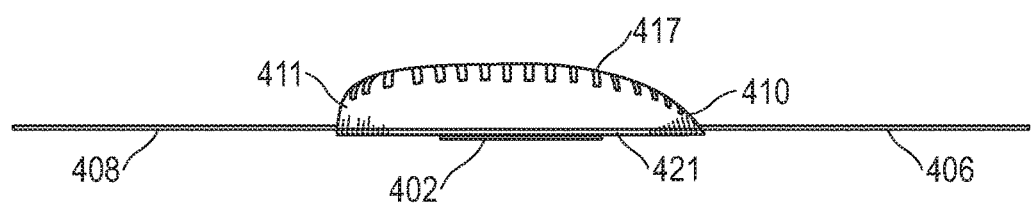
FIG. 9 is a side edge view of an embodiment of the invention.

It is also suitable to have the sole sloped only to the front, the front will be tapered as shown but the rear will be essentially flat (but rounded) from the center of the member to allow more stable footing as is illustrate in FIGS. 7, 8 and 9. This rocker configuration provides the equine a more stable footing in a preferred neutral resting position. The neutral resting position in the rear section of the device enables the horse to have a stable place to rest, yet if there is movement fore and aft the hoof or laterally the rocker rolls to lessen torque on the tendons, ligaments and especially on compromised lamina. This configuration is generally preferred.

Both configurations are useful in appropriate situations and both are within the scope of this invention. The narrowed toe of the rocker base (as illustrated in the Figures) enhances lateral break-over and provides the equine with more flexibility of movement. Various ways in which this solid member may be tapered are within the scope of this invention. A number of possible rocker shapes are described in co-pending U.S. published application. 2011/0067366, Mar. 24, 2011 (Ser. No. 12/882,352), incorporated herein by reference for all purposes. The sloped shape on the bottom moves the break-over point back as well as helping isolate the lateral forces on the cast and thereby on the bone column.

An advantage of the sloped base of the shoe is that it greatly reduces the surface area in contact with the ground or other surface onto which the equine stands. For example, a typical hoof bottom would be, for example, about 8 inches×8 inches or 64 square inches. A suitable shoe sole will be about 4 inches×5 inches or 20 square inches which is only about 30% of the surface of the hoof bottom. Smaller rockers will reduce the ground contact even further.

The shoe shape of this invention is designed and sized to provide the optimum break-over for most applications; however, when the solid structure is constructed of a molded elastomer it may also be customized on site of use to an individual equine or individual need with standard farrier tools such as a rasp and knives. Molded elastomer enables an attending practitioner to further customize the device for each patient after looking at radiographs or other imaging means to the position of the coffin bone relative to the ground level and watch the horse's movement with the device. The upper harder section of the shoe (121 and 421 in the Figures) is suitably made from harder elastomer such as polyurethane with a Shore A hardness of about 90 to 95 or more. It should not be so hard as to be brittle and easily broken but hard enough to provide good support and dimensional stability the lower softer section. The lower section of the solid member (111, 211 and 411 in the figures) is preferably made of molded elastomeric polymer. It needs to be relatively hard and rigid, but not completely so. Molded polyurethane is very suitable and convenient to work with. It is preferred that thermoplastic polyurethane of about 55 to Shore A hardness be used, with Shore A hardness of about 45 to 65 being preferred. The important point is that the hardness can be adapted to the individual need of the horse to which it is applied. Polyurethanes are easily moldable in open molds or by injection molding. Other polymer materials with similar characteristics as polyurethane, such as polyvinyl chlorides, styrene butadiene styrene polymer, epoxies and the like, are also usable. Choice of these will be well within the ability of those skilled in the polymer art to select.

In another embodiment the solid member is made in two separate pieces—one more rigid section with the straps attached and a shaped shoe attached to the more rigid solid support member. This embodiment is illustrated in FIG. 12 of US published application U.S. 2015/0088042, published Mar. 26, 2015 (incorporated herein by reference) where part 405 is the rigid solid member and 410 the attachable shoe straps 402, 406 and 408 are shown. As shown, the, 410 (having the same two-density structure as described above with 411 lower section and 411 harder upper section), is attached to the solid member base 405, by barrel screws (415 and 416), but it may also be attached in other ways as by adhesives, horse shoe nails, direct bonding and the like. A suitable solid member base in a two piece arrangement will be polyurethane of a Shore A hardness of 90 harder.

In applying the shoe it is often desirable that hoof frog support be provided. This may be accomplished by uses of a number of currently available filers known in the art. Hover, in one embodiment a suitable frog support is provided in this invention as illustrated in FIG. 10. The support, 424 is a triangular shape (as is the frog of an equine hoof) It can be molded into the shoe top surface as an integral part thereof or can be a separate piece that is attached as with a suitable adhesive. Polyurethane-casting elastomer having a Shore A hardness of from about 8 to about 50 is suitable for the frog support but very soft support may also be desirable in some cases, having a Shore 00 hardness of about 5 to 70.

The lower section of the shoe, if made of polymer, may be reduced in weight by adding low density small particles (preferably spheroidal shaped) into the polymer as is done with polymer equine boot orthotics in U.S. patent application Ser. No. 13/396,191, filed Feb. 14, 2012, and U.S. patent Ser. No. 14/046,430 filed Oct. 4, 2013, the disclosures of which is incorporated herein by reference. The particles may be any material with sufficient flexibility and durability for incorporation into a shock absorbing orthotic pad. In a preferred embodiment wherein the polymer of the solid member is polyurethane, the particles materials are of lower density than elastomeric polyurethane, capable of being adhered to by elastomeric polymer materials (preferably polyurethane), and generally spherical or elliptical in shape. Suitable materials may include, but are not limited to, polymers and elastomers, and preferably expanded foam or cellular formulation of these polymers. Specific examples include polypropylene and expanded polypropylene (PP), polyethylene and expanded polyethylene (PE), high density polyethylene (HDPE), ethylene propylene diene monomer (EPDM), polystyrene (PS), polyurethane and polyurethane foams, polystyrene, polybutadiene, styrene-butadiene rubber (SBR), and polyvinyl chloride. In one embodiment, polypropylene and polyethylene are preferred, with closed-cell expanded polypropylene being particularly preferred for its low density, high durability, flexibility, resilience, and thermal insulation. The particle cross section or diameters are desirably in the range of one (1) to six (6) millimeters (mm) ($3.9 \times 10^{-2}$ to $2.4 \times 10^{-1}$ inches). In a preferred embodiment, the spheroids have a diameter of approximately two (2) to four (4) mm ($7.9 \times 10^{-2}$ to $1.6 \times 10^{-1}$ inches), with approximately three (3) mm ($7.9 \times 10^{-2}$ inches) being particularly preferred. Particles of these sizes are small enough to be incorporated into the elastomer and large enough to not unduly increase viscosity of the polymer mixture during molding. If the particles are too large the result is a kind of permanent set reducing the flexibility and compressibility of the molded piece. One of the key properties of the particles is their low density compared to the polymer of the solid member, resulting in a lower overall weight-to-volume ratio of the member. The difference in density between the particles and the polymer causes the particles to rise towards the top of the mold during casting, which becomes the bottom of the member. Because the particles are lower density than the polymer, they rise and accumulate at the top of the mold, which is the bottom of the pad, during molding. The member will then consist of a top layer comprised predominately of elastomer(s) that will be in contact with the hoof and a bottom layer of particle-filled polymer that provides a thermal barrier to protect the bottom of the cast, on which the device is fitted, from overheating. It is obvious that in other embodiments, the relative densities of the particles and elastomer(s) may be varied to control the relative positions of elastomer and particles. The density of the particles is desirably in the range of about twenty (20) to five hundred twenty (520) grams/liter (g/l). For example, expanded polypropylene beads have a density range of about ten to two hundred (10-200) g/l, and preferred mid density beads have a density range of from about forty to one hundred twenty (40-120) g/l. Suitable polyurethane elastomers have densities of about one thousand twenty-five to one thousand seventy (1025-1070) g/l, so the ratio of density of elastomer to particle will be in the range of from about eight to twenty-eight (8-28). It is preferred that the particles be at least half the density of the elastomer and preferably no more than about 30% as dense.

The invention has been described herein by several embodiments but it will be evident that various modifications and changes can be made thereto without departing from the broader spirit and scope of the invention as set forth in the appended claims. The specification is, accordingly, to be regarded in an illustrative rather than a restrictive sense and the scope of the invention should be limited only by the appended claims.

The invention claimed is:

1. An equine shoe comprising a dual density, solid member that covers substantially the entire underside of a hoof, and having a top surface and a bottom surface and having fabric straps attached to the solid member and extending from at least two sides of the solid member, wherein the solid member has two sections being a higher density top layer of hard material of at least Shore A 90 and a lower density lower layer of less hard material with a Shore A hardness of about 45 to 65, the top layer providing support and dimensional stability to the softer lower layer, and wherein the bottom surface of the solid member is patterned.

2. The shoe of claim 1 wherein the solid member provides a rocker effect, having a front and rear, and wherein the bottom surface is generally sloped from approximately the centerline of the member toward the front and rear.

3. The shoe of claim 1 wherein the solid member provides a rocker effect, having a front and rear, and wherein the bottom surface is generally sloped toward the front and rounded at the rear, the slope being from approximately the centerline of the member.

4. The shoe of claim 1 wherein the straps are made of nylon ballistic cloth or ultra-high-molecular-weight polyethylene fabrics and wherein the straps are incorporated into at least one section of the solid member during molding of the solid member.

5. The shoe of claim 1 wherein the solid member is made of polyurethane.

6. The shoe of claim 1 wherein the solid member has a topside and underside and the underside of the solid member is at least partially patterned by a series of ridges and grooves at least partially parallel to one another.

7. The shoe of claim 1 wherein the solid member has four sides and the straps extend from four sides of the solid member, and wherein the straps are incorporated into at least one section of the solid member during molding of the solid member, the straps configured to extend from the four sides of the solid member by laying two pieces of strap material at an angle relative to the length of one another and generally flat and parallel relative to the top surface of the solid member.

8. The shoe of claim 1 wherein the solid member has incorporated into at least one section thereof particles of lower density than that of the section the particles are incorporated into, to reduce the total weight of the solid member.

9. The shoe of claim 1 also comprising a separated rocker member adapted to be attached to the bottom surface of the solid member.

10. A method of shoeing an equine animal by placing on its hooves shoes comprising a dual density, solid member that covers substantially the entire underside of a hoof, and having a top surface and a bottom surface and having fabric straps attached to the solid member and extending from at least two sides of the solid member, wherein the solid member has two sections, being a higher density top layer of hard material of at least Shore A 90 and a lower density lower layer of less hard material of Shore A hardness of about 45 to 65, the top layer providing support and dimensional stability to the softer lower layer, and wherein the bottom surface of the solid member is patterned.

11. The method of claim 10 wherein the solid member provides a rockered effect, having a front and rear and wherein the bottom surface is generally sloped toward the front and rear.

12. The method of claim 10 wherein the straps are made of nylon ballistic cloth or ultra-high-molecular-weight polyethylene fabrics and the solid member is made of polyurethane, and wherein the straps are incorporated into at least one section of the solid member during molding of the solid member, the straps configured to extend from four sides of the solid member by laying two pieces of strap material at an angle relative to the length of one another and generally flat and parallel relative to the top surface of the solid member.

13. The method of claim 10 wherein the shoe is secured to the hoof by placing the straps alongside the hoof and leg of the animal and wrapping with casting tape.

14. The method of claim 10 wherein the shoe is secured to the hoof with nails or adhesive.

15. The method of claim 10 wherein the shoe is secured to the hoof by providing hook and loop connector halves to the straps and attaching the hook and loop connector halves together around the equine animal's hoof.

16. A dual-density equine shoe comprising a solid member that covers substantially the entire underside of a hoof, and having a top surface and a bottom surface and having fabric straps attached to the solid member and extending from at least two sides of the solid member, wherein the solid member is of higher density, being of a hard material of at least Shore A 90, the shoe further comprising a separated rocker member of lower density, being of less hard material with a Shore A hardness of about 45 to 65 and adapted to be attached to the bottom surface of the solid member, wherein the solid member provides support and dimensional stability to the softer separated rocker member, and wherein the bottom surface of the separated rocker member is patterned.

17. The shoe of claim 16 wherein the straps are made of nylon ballistic cloth or ultra-high-molecular-weight polyethylene fabrics, and wherein the solid member has four sides and the straps extend from four sides of the solid member, and wherein the straps are incorporated into at least one section of the solid member during molding of the solid member, the straps configured to extend from the four sides of the solid member by laying two pieces of strap material at an angle relative to the length of one another and generally flat and parallel relative to the top surface of the solid member.

18. The shoe of claim 16 wherein the separated rocker member has incorporated therein particles of lower density than that of the separated rocker member, to reduce the total weight of the separated rocker member.

19. The shoe of claim 16 wherein the separated rocker member has a front, a rear, and a bottom surface, and wherein the bottom surface is generally sloped from approximately the centerline of the separated rocker member toward the front and rear.

20. The shoe of claim 16 wherein the separated rocker member has a front, a rear, and a bottom surface, and wherein the bottom surface is generally sloped toward the front and rounded at the rear, the slope being from approximately the centerline of the member.

* * * * *